(12) United States Patent
Raman et al.

(10) Patent No.: US 9,018,389 B2
(45) Date of Patent: Apr. 28, 2015

(54) PROCESS FOR THE PREPARATION OF DEFERASIROX

(75) Inventors: Jayaraman Venkat Raman, Vadodara (IN); Hiral Shah, Vadodara (IN)

(73) Assignee: Alembic Pharmaceuticals, Ltd., Gujarat, Vadodara (IN)

( * ) Notice: Subject to any disclaimer, the term of this patent is extended or adjusted under 35 U.S.C. 154(b) by 42 days.

(21) Appl. No.: 13/988,361

(22) PCT Filed: Nov. 4, 2011

(86) PCT No.: PCT/IB2011/054916
§ 371 (c)(1),
(2), (4) Date: Oct. 18, 2013

(87) PCT Pub. No.: WO2012/069946
PCT Pub. Date: May 31, 2012

(65) Prior Publication Data
US 2014/0039199 A1    Feb. 6, 2014

(30) Foreign Application Priority Data

Nov. 24, 2010 (IN) .......................... 3214/MUM/2010

(51) Int. Cl.
*C07D 249/08* (2006.01)
(52) U.S. Cl.
CPC .................................. *C07D 249/08* (2013.01)

(58) Field of Classification Search
USPC ....................................................... 548/269.2
See application file for complete search history.

(56) References Cited

U.S. PATENT DOCUMENTS 6,465,504 B1    10/2002    Lattmann et al.

FOREIGN PATENT DOCUMENTS

| EP | 1 927 591 A1 | 6/2008 |
|----|----|----|
| WO | 97/49395 | 12/1997 |
| WO | 2008/065123 A2 | 6/2008 |
| WO | 2009/094956 | 8/2009 |
| WO | 2009/130604 A1 | 10/2009 |

OTHER PUBLICATIONS

International Search Report dated Feb. 8, 2012, in PCT/IB2011/054916.
Written Opinion dated Apr. 2005, in PCT/IB2011/054916.
Applicant's response to the Written Opinion in PCT/IB2011/054916, dated Apr. 4, 2012.

*Primary Examiner* — Rebecca Anderson
*Assistant Examiner* — Karen Cheng
(74) *Attorney, Agent, or Firm* — McAndrews Held & Malloy, Ltd.

(57) ABSTRACT

The present invention provides improved process for the preparation of Deferasirox of formula (I).

5 Claims, No Drawings

PROCESS FOR THE PREPARATION OF DEFERASIROX

CROSS REFERENCE TO RELATED APPLICATIONS

This application is a U.S. national stage entry of International Patent Application Serial No. PCT/IB2011/054916, filed on Nov. 4, 2011, which claims priority of Indian Patent Application Serial No. 3214/MUM/2010, filed on Nov. 24, 2010.

FIELD OF INVENTION

The present invention relates to an improved, commercially viable and industrially advantageous process for the preparation of Deferasirox of formula (I) in high yield and purity.

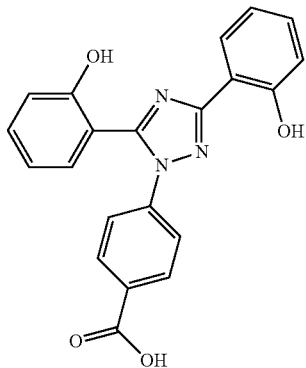

Formula I

BACKGROUND OF THE INVENTION

Deferasirox is chemically known as 4-[3,5-bis(2-hydroxyphenyl)-[1,2,4]triazol-1-yl]benzoic acid. It is a rationally-designed oral ironchelator. Its main use is to reduce chronic iron overload in patients who are receiving long-term blood transfusions for conditions such as beta-thalassemia and other chronic anemias. The current pharmaceutical product containing this drug is being sold by Novartis using the tradename Exjade® in the form of tablets.

U.S. Pat. No. 6,465,504 discloses a process for preparing Deferasirox wherein the process includes reacting salicyloyl chloride with salicylamide at 170° C. to obtain 2-(2-hydroxyphenyl)benz[e][1,3]oxazin-4-one, and further crystallization in ethanol to obtain slight yellow color crystals of 2-(2-hydroxyphenyl)benz[e][1,3]oxazin-4-one. 2-(2-hydroxyphenyl)benz[e][1,3]oxazin-4-one which is further reacted with 4-hydrazinebenzoic acid in presence of ethanol to give Deferasirox. Major drawback of this process is preparation of 2-(2-hydroxyphenyl)benz[e][1,3]oxazin-4-one at high temperature and in the absence of solvent which causes formation of several impurities which is difficult to avoid.

U.S. Pat. No. 6,465,504 disclose process for the preparation of Deferasirox which require unwieldy steps for the preparation and purification of Deferasirox. The reaction conditions employed for the production of Deferasirox results in formation of large amount of impurities.

WO2009/094956 disclose the process for preparing Deferasirox where in the process includes the reaction of 2-(2-hydroxyphenyl)benz[e][1,3]oxazin-4-one with 4-hydrazinebenzoic acid is carried out in the presence of organic acid such as C1 to C4 carboxylic acid.

Therefore, there is a need of process for the preparation of Deferasirox which not only devoid disadvantages of prior process as mentioned hereinabove but also gives high yield and purity of Deferasirox. The process of present invention overcomes disadvantages of prior process and gives high yield and purity of Deferasirox.

Object of the Invention

The object of the present invention is to provide improved process for the preparation of Deferasirox which gives Deferasirox with greater yield and purity and also process for the preparation of Deferasirox form I.

The object of the present invention is to provide improved process for the preparation of Deferasirox comprising step of treating 2-(2-hydroxyphenyl)benz[e][1,3]oxazin-4-one with 4-hydrazinebenzoic acid in the presence of dehydrating agent, suitable solvent and optionally in the presence of water.

Further object of the present invention is to provide a purification process for preparation of highly pure Deferasirox comprising
  a) Suspending Deferasirox in a solvent selected from the group consisting of polar organic solvent.
  b) Adding 30% $H_2O_2$ and water.
  c) Heat the said reaction mass at 25-35° C. optionally.
  d) Filter the reaction mass and wash it with water.
  e) Charge the wet cake in water and stirred at 55-85° C.
  f) Filter the solid product and wash it by water to get pure Deferasirox substantially free of hydrazine impurity.

Further object of present invention is to provide a process for preparation of Deferasirox Form I
  a) Suspending Deferasirox in a Methanol:Ethyl acetate mixture.
  b) Heat the said solution.
  c) Optionally, subjecting the said solution to carbon treatment or silica gel treatment.
  d) Add water and heat the said solution.
  e) Partially removing the solvent from the solution
  f) Precipitating pure Deferasirox form I.

DETAILED DESCRIPTION OF THE INVENTION

The present invention provides a process for preparation of Deferasirox which comprises: reacting 2-(2-hydroxyphenyl)benz[e][1,3]oxazin-4-one with 4-hydrazinebenzoic acid in the presence of dehydrating agent such as potassium hydrogen sulphate, sodium hydrogen sulphate and the like or mixture thereof in suitable solvent and optionally in the presence of water.

In another embodiment of the present invention provides a purification process for preparation of highly pure Deferasirox comprising
  a) Suspending Deferasirox in a solvent selected from the group consisting of polar organic solvent preferably from Dimethyl sulfoxide, Dimethyl formamide, Hexamethyl phosphorotriamide, Tetrahydrofuran
  b) Adding 30% $H_2O_2$ and water.
  c) Heat the said reaction mass at 25-35° C. optionally.
  d) Filter the reaction mass and wash it with water.
  e) Charge the wet cake in water and stirred at 55-85° C.
  f) Filter the solid product and wash it by water to get pure Deferasirox substantially free of hydrazine impurity.

Further embodiment of present invention is to provide a process for preparation of Form I of Deferasirox a) Suspending Deferasirox in a Methanol:Ethyl acetate mixture.
b) Heat the said solution.
c) Optionally, subjecting the said solution to carbon treatment or silica gel treatment.
a) Add water and heat the said solution.
b) Partially removing the solvent from the solution.
c) Precipitating pure Deferasirox form I.

The term 'dehydrating agent' as used hereinabove includes but not limited to a reagent which absorbs water formed during reaction and avoids contamination of water which causes further progress of reaction. These includes but not limited to potassium hydrogen sulphate, sodium hydrogen sulphate and the like or mixture thereof.

The term suitable solvent as used here in above includes any alcoholic solvent containing $C_1$-$C_8$ carbon atom.

The embodiments of present invention are shown in below given scheme.

The process for preparation of Deferasirox is shown in the scheme I.

The present invention further illustrated in detail by the below examples which are however not limit to the scope of the invention.

EXAMPLE-I

Preparation of 2-(2-Hydroxyphenyl)Benz[e][1,3]Oxazin-4-One

Xylene (1.5 L) and salicylic acid (1 Kg.) was added to a 5 L 4-neck round bottom flask equipped with a mechanical stirrer and thermocouple. Thionyl chloride (1.29 kg) was added at 10° C. to 15° C. After addition of thionyl chloride reaction mass is stirred at 10° C. to 15° C. for 30 minutes. Reaction mass is heated at 35-40° C. for 1 hr. Salicylamide solution (0.891 kg in 2.0 lit of Xylene) was added in reaction mass at 25° C.-30° C. After addition reaction mass was gradually heated at 80° C.-126° C. and stirred for 2 hrs. After the completion of reaction excess of Xylene was distilled out.

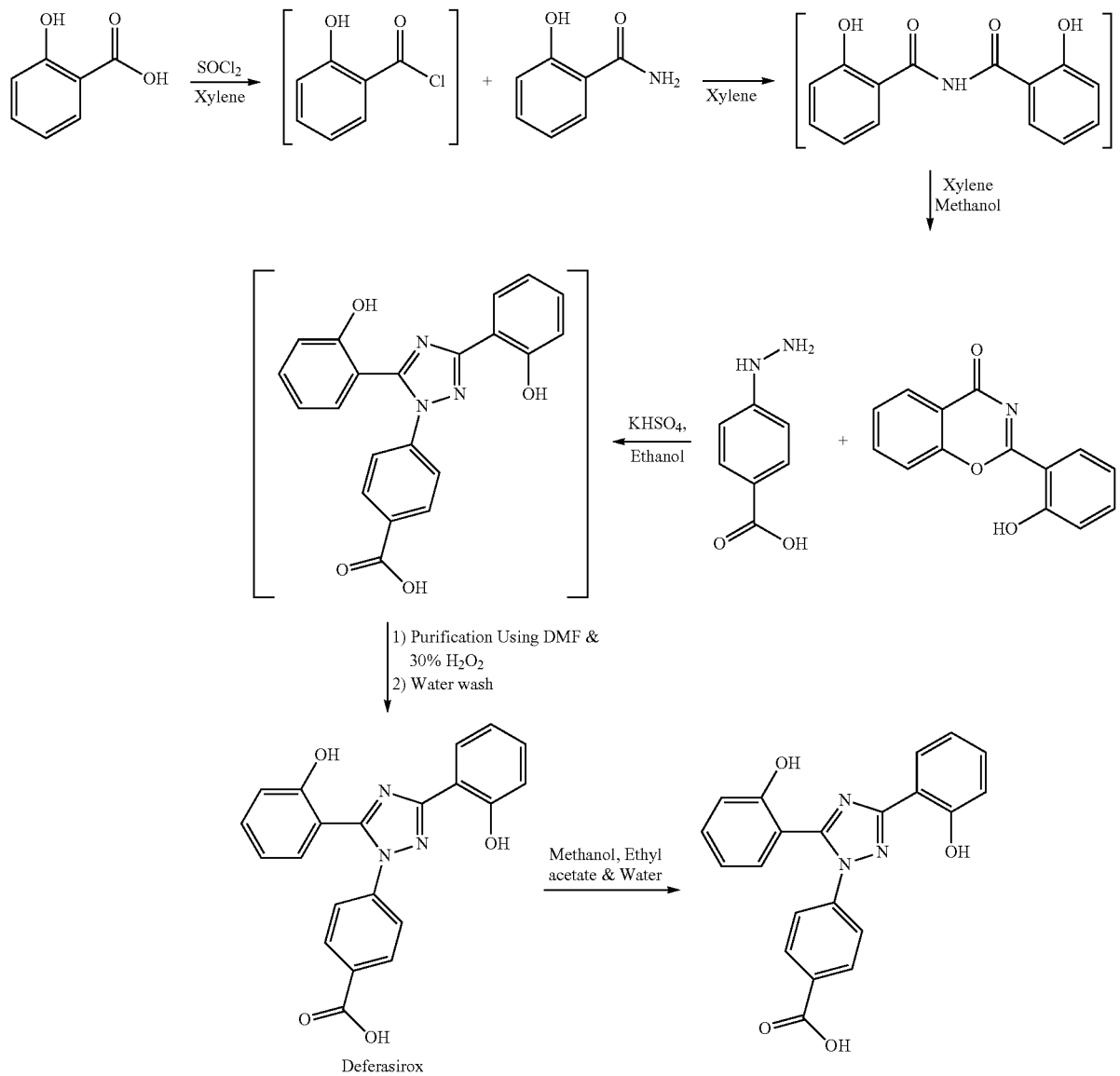

Deferasirox

Methanol was added in the reaction mass at 70° C.-80° C. and stirred for 1 hr. gradually cooled the reaction mass at 25-30° C. Filtered the solid and washed with Methanol and sucked it dry. Dry the obtained solid at 55-60° C. under vacuum tray drier.

EXAMPLE-II

Preparation of Deferasirox 2-(2-hydroxyphenyl)benz[e][1,3]oxazin-4-one (1.0 kg) and 4-Hydrazino benzoic acid (0.699 kg), Ethanol (9.0 lit), Water (1.0 lit) was stirred at 25-35° C. in round bottom flask. Followed by addition of Potassium hydrogen sulphate (0.15 kg) into the reaction mass and heated the reaction mass at 70-75° C. for two hrs. Cooled the reaction mass at 25-30° C. and stirred for 45 minutes. Filtered off the solid and washed with ethanol. Obtained solid and water (1.0 lit) stirred at 25-30° C. for 15 minutes and then heated at 50-55° C. for 1 hr. The solid was filtered at 50-55° C. and washed with water. Charge this wet cake in DMF (5.0 lit) and stirred at 25-30° C. In this solution 30% $H_2O_2$ was added at 25-30° C. within 1 hr. Followed by addition of water at 25-30° C. and stirred for 30 minutes. Filtered off the solid and washed it with water. The obtained solid was added in pre heated water and stirred at 45-50° C. Gradually increased the temperature up to 65-75° C. & stir it for 60 min. cooled the reaction mass at 45-50° C. and stirred it for 40 minutes. The precipitated Deferasirox filtered off and washed with water. Dry the solid at 65-75° C. in vacuum tray drier.

EXAMPLE III

Preparation of Form I of Deferasirox

Crude Deferasirox was suspended in Methanol:Ethyl acetate (1:1) (2.2 L) mixture. Followed by heating at 65-75° C. until obtaining a clear solution. Activated carbon was added to the reaction mass and heated for 20 minutes at 65-70° C. Cooled the reaction mass at 45-50° C. and filtered off through hyflow. Again reaction mass is heated at 65-70° C. followed by addition of process water at 65-70° C. and stirred for 15 minutes. The solvent was distilled out at 65-80° C. Cooled the reaction mass at 25-30° C. and stirred for 45 minutes. The precipitated Deferasirox filtered off and washed with water. Dry the form I of Deferasirox at 65-70° C. in vacuum tray drier.

The invention claimed is:

1. A method for preparing Deferasirox comprising the step of: treating 2-(2-hydroxyphenyl)benz[e][1,3]oxazin-4-one with 4-hydrazinobenzoic acid in the presence of potassium hydrogen sulfate, sodium hydrogen sulfate, or a mixture thereof, a suitable solvent, and optionally in the presence of water.

2. The method of claim 1, wherein the suitable solvent is a $C_1$-$C_8$ alcohol.

3. The method of claim 1, further comprising purifying Deferasirox, the purifying comprising:
   (i) suspending Deferasirox in a polar organic solvent to provide a suspension;
   (ii) adding 30% $H_2O_2$ and water to the suspension to provide a reaction mass; and
   (iii) filtering the reaction mass to provide purified Deferasirox.

4. The method of claim 3, wherein the polar organic solvent comprises dimethylsufoxide, dimethylformamaide, hexamethylphosphorotriamide, or tetrahydrofuran.

5. The method of claim 4, wherein the polar organic solvent comprises dimethylformamide.

* * * * *